United States Patent
Fischer et al.

(10) Patent No.: US 10,772,747 B2
(45) Date of Patent: Sep. 15, 2020

(54) VASCULAR IMPLANT WITH ASYMMETRICAL STENT SPRINGS

(71) Applicant: JOTEC GmbH, Hechingen (DE)

(72) Inventors: Heike Fischer, Meerbusch (DE); Juergen Merz, Balingen (DE)

(73) Assignee: JOTEC GmbH (DE)

( * ) Notice: Subject to any disclaimer, the term of this patent is extended or adjusted under 35 U.S.C. 154(b) by 0 days.

(21) Appl. No.: 14/717,922

(22) Filed: May 20, 2015

(65) Prior Publication Data

US 2015/0250629 A1 Sep. 10, 2015

Related U.S. Application Data

(63) Continuation of application No. PCT/EP2013/074366, filed on Nov. 21, 2013.

(30) Foreign Application Priority Data

Nov. 21, 2012 (DE) .................. 10 2012 111 223

(51) Int. Cl.
   *A61F 2/86* (2013.01)
   *A61F 2/07* (2013.01)
   *A61F 2/89* (2013.01)

(52) U.S. Cl.
   CPC .................. *A61F 2/89* (2013.01); *A61F 2/07* (2013.01); *A61F 2002/075* (2013.01); *A61F 2250/0037* (2013.01)

(58) Field of Classification Search
   CPC ........ A61F 2/07; A61F 2/82; A61F 2002/072; A61F 2002/075; A61F 2/06; A61F 2/86;
   (Continued)

(56) References Cited

U.S. PATENT DOCUMENTS

| 2003/0208260 A1 | 11/2003 | Lau et al. |
| 2005/0043782 A1* | 2/2005 | Gomez ..................... A61F 2/91 623/1.16 |

(Continued)

FOREIGN PATENT DOCUMENTS

| WO | WO 2006/125382 A1 | 11/2006 |
| WO | WO 2008/051543 A2 | 5/2008 |

(Continued)

OTHER PUBLICATIONS

International Search Report from parent PCT Application No. PCT/EP2013/074366, 5 pages (dated Feb. 3, 2014)(in German, with English Translation 3 pages).

(Continued)

*Primary Examiner* — Ann Schillinger
(74) *Attorney, Agent, or Firm* — Klarquist Sparkman, LLP

(57) ABSTRACT

The invention relates to a self-expanding vascular implant for implanting into a blood vessel, the implant comprising a hollow cylindrical body with a proximal and a distal end and with a longitudinal axis; comprising stent springs, which are successively arranged and spaced from one another over the longitudinal axis of the body, each stent spring meandering; and comprising an implant material, which is fixed to the stent springs and connects same. The stent springs have pointed arches which alternately point toward the proximal and distal direction and comprise alternating crests and troughs that are connected to one another via legs of different lengths, whereby a stent spring has pointed arches, which are circumferentially and successively arranged and which have different heights, said pointed arches consisting of higher and shorter pointed arches.

11 Claims, 5 Drawing Sheets

(58) Field of Classification Search
CPC .... A61F 2/89; A61F 2/915; A61F 2002/2835; A61F 2002/821; A61F 2002/825; A61F 2002/91516; A61F 2002/91533; A61F 2002/91541; A61F 2230/0069
See application file for complete search history.

(56) References Cited

U.S. PATENT DOCUMENTS

| | | | | |
|---|---|---|---|---|
| 2007/0055347 | A1* | 3/2007 | Arbefeuille | A61F 2/07 623/1.15 |
| 2008/0114441 | A1* | 5/2008 | Rust | A61F 2/07 623/1.13 |
| 2008/0114445 | A1* | 5/2008 | Melsheimer | A61F 2/07 623/1.13 |
| 2008/0195191 | A1* | 8/2008 | Luo | A61F 2/07 623/1.13 |
| 2010/0011976 | A1 | 1/2010 | Armstrong et al. | |
| 2010/0011979 | A1 | 1/2010 | Armstrong et al. | |
| 2011/0218617 | A1 | 9/2011 | Nguyen et al. | |
| 2011/0319983 | A1 | 12/2011 | Zhu et al. | |

FOREIGN PATENT DOCUMENTS

| | | |
|---|---|---|
| WO | WO 2008/051543 A3 | 5/2008 |
| WO | WO 2012/061526 A2 | 5/2012 |
| WO | WO 2012/061526 A3 | 5/2012 |

OTHER PUBLICATIONS

Office action mailed by the Japan Patent Office dated Jul. 26, 2016, for Japanese Patent Application No. 2015-543422. In Japanese, with attached English-language translation (7 pages).

\* cited by examiner

VASCULAR IMPLANT WITH ASYMMETRICAL STENT SPRINGS

CROSSREFERENCES TO RELATED APPLICATIONS

This application is a continuation of international patent application PCT/EP2013/074366, filed on Nov. 21, 2013, designating the U.S., which international patent application has been published in German language and claims priority from German patent application DE 10 2012 111 223.1, filed on Nov. 21, 2012. The entire contents of these priority applications are incorporated herein by reference.

BACKGROUND OF THE INVENTION

The present invention relates to a self-expanding vascular implant for implanting into a blood vessel, comprising a hollow-cylindrical body with a first end and a second end and a longitudinal direction, and also comprising stent springs successively arranged at a distance from one another over its longitudinal axis and circumferentially meandering, respectively, and comprising an implant material fixed to the stent springs and connecting them, the stent springs only being connected via the implant material and not between one another, and the circumferential stent springs having pointed arches facing alternately toward the proximal direction and the distal direction and having alternating vertices and lowest points, which are connected to one another by legs.

Such vascular implants are known in the prior art, e.g. from DE 103 37 739.5.

For treatment of aneurysms in arteries, it is generally known to implant intraluminal vascular implants, which are also referred to as endovascular stents/stent grafts. An aneurysm is understood as being a widening or bulging of an arterial blood vessel as a result of congenital or acquired changes of the wall. The bulging may affect the vessel wall as a whole or, as in the case of a so-called false aneurysm or so-called dissection, blood can flow from the lumen of the artery in between the layers of the vessel wall and can tear them apart. Non-treatment of an aneurysm can lead to a rupture of the artery at the advanced stage, with the consequence that the patient internally bleeds.

The self-expanding vascular implants that are used for the treatment of such aneurysms generally consist of a hollow-cylindrical metal frame, the lateral surface of which is covered with a textile or polymer film, so that a hollow-cylindrical body is obtained. For implantation, the vascular implant is radially compressed, so that its cross section is significantly reduced. Then, with the aid of an insertion system, the vascular implant is brought into the region of the aneurysm, where it is released. Due to the resilience of the metal frame, the vascular implant expands again into its original form, thereby spreading its jacket surface, which becomes clamped internally in the blood vessel proximally and distally with respect to the aneurysm. In this way, the blood can now flow through the vascular implant and further loading of the bulging is prevented.

The metal frame of such vascular implants generally consists for example of a wire mesh or of so-called stent springs successively arranged one behind the other and circumferentially meandering, which are—as the case may be—connected to one another by way of connecting supports of wire, or which are only connected to one another via the implant material. The wire mesh or the stent springs are usually of a shape-memory metal, generally of nitinol, whereby, after being introduced into a vessel, the stent springs again transition into the expanded state for release, and thereby "spread out" the vascular implant.

With vascular implants known in the prior art, in particular those that have stent springs circumferentially meandering, which are either only connected to one another by implant material, and consequently only indirectly connected, or else are additionally connected between one another by way of connecting legs or supports, there is the risk of kinking/buckling during the introduction into a vessel, and in particular whenever the vascular implant is introduced into or through a bent portion of a vessel. This kinking occurs in particular whenever the vascular implant is intended to be adapted to the natural shape of the bent vessel, and the bend is intended to run in the region of two or more stent springs arranged one behind the other: in this region, a lowest point of the one stent spring and a vertex of the stent spring arranged distally thereafter usually lie opposite one another, so that the vascular implant easily buckles here on account of the small intermediate space that lies between these two points and is only formed by the implant material.

Such kinking/buckling is extremely disadvantageous, since the regular blood flow through the vessel is no longer ensured when there is kinking, and, as a consequence, stenoses and turbulences of the blood within the vascular implant may occur or even a vessel occlusion.

SUMMARY OF THE DISCLOSURE

Therefore, the object of the present invention is to provide a vascular implant by means of which the risk of kinking of the vascular implant can be avoided, or at least reduced to the greatest extent, while retaining the longitudinal stability of the vascular implant.

This object is achieved according to the invention by a development of the vascular implant mentioned at the beginning in which at least two stent springs successively arranged one behind the other in the longitudinal direction, respectively, have legs of different lengths for forming of pointed arches of varying height circumferentially following one another, with higher and shorter pointed arches, and that a higher pointed arch, facing toward the proximal direction, of a first stent spring lies opposite a shorter pointed arch, facing toward the distal direction, of a second stent spring arranged proximally thereafter, at a distance and at an imaginary line that runs parallel to the longitudinal axis of the vascular implant.

Due to the design of different leg lengths, and the thus pointed arches of varying height facing alternately in the proximal direction and the distal direction, the overall shape of a stent spring is asymmetrical. The stent springs, at least two, preferably all of the stent springs of a vascular implant, consequently have irregular "amplitudes", i.e. pointed arches that vary in height due to the legs being of varying length. Therefore, according to the invention, higher and shorter pointed arches are formed alternately in the circumferential direction of the stent springs. Presently, the terms "varying height" and "higher" and "shorter" are intended to relate to the relationship of the pointed arches to one another. The highest pointed arch of a stent spring therefore has a leg that is longest with respect to other legs of the same stent spring. The length of the longest leg of a stent spring consequently also predetermines the height of the stent spring, that is to say the stent spring height. It goes without saying that—although the lengths of legs following one another directly differ—one stent spring can have a number of legs of the same length, the succession of which is however by definition interrupted by legs of other lengths.

The combination of these asymmetrical stent springs with the arrangement of at least two stent springs arranged one behind the other in such a way that a higher pointed arch, facing toward the proximal direction, of a first stent spring lies opposite a shorter pointed arch, facing toward the distal direction, of a second stent spring arranged thereafter in the distal direction advantageously achieves the effect that bending of the vascular implant according to the invention in a vessel does not lead to buckling, or this buckling is avoided to the greatest extent or can only occur in the case of significantly smaller radii, and the risk of kinking is highly decreased. Due to the fact that a higher pointed arch, facing toward the proximal direction, of a first stent spring lies opposite a shorter pointed arch, facing toward the distal direction, of a second stent spring arranged proximally thereafter, at a distance and at an imaginary line that runs parallel to the longitudinal axis of the vascular implant, the longitudinal/axial stiffness is good, along with high flexibility. Under bending, long and short vertices quasi engage with one another. As a result, the stent graft is also very flexible in three dimensions.

The pointed arches facing alternately toward the proximal direction and toward the distal direction may also be referred to, in other terms, as "wave crests" and "wave troughs", a "wave crest" referring to a pointed arch facing toward the proximal direction and a "wave trough" referring to a pointed arch facing toward the distal direction. In the described embodiment, an asymmetrical meandering shape of the circumferential stent springs is achieved, with two successive wave crests—or pointed arches facing toward the proximal direction—having different heights, respectively, and consequently also with the wave troughs—or pointed arches facing toward the distal direction—lying there between having different depths. Thus, in an alternating manner in circumferential direction, a higher wave crest/vertex is followed by a wave crest/vertex that is lower or less high than the previous wave crest/vertex, and this wave crest/vertex is again followed by a wave crest/vertex that is higher than the wave crest/vertex directly before it, and so on, whereby wave troughs/lowest points of respectively varying depth lying between the wave crests/vertices of varying height: also with respect to the wave troughs/lowest points, a lower wave trough/lowest point is again followed in an alternating manner in the circumferential direction by a wave trough/lowest point that is less low than the wave trough/lowest point arranged directly before it in the circumferential direction, and this wave trough/lowest point is again followed by a wave trough/lowest point that is lower than the one before it. In other words, a stent spring therefore has pointed arches with at least two or three lowest points of varying depth, the different depths relating to an imaginary line that runs around perpendicularly in relation to the longitudinal axis of the hollow-cylindrical main body and connects the lowest lowest points to one another. By definition, consequently, less low lowest points do not lie on this imaginary line, and the same applies in turn to the vertices.

Likewise in other terms, in accordance with the vascular implant according to the invention, at least two stent springs successively arranged over the longitudinal axis are arranged with respect to the longitudinal axis of the hollow-cylindrical main body and with respect to one another, such, that the lowest points of the pointed arches of a first stent spring respectively lie opposite the vertices of pointed arches of a second stent spring arranged after the first stent spring in the longitudinal axis of the vascular implant at a distance and at an imaginary line that runs parallel to the longitudinal axis of the vascular implant, and more precisely, such, that a lowest of a lowest point of a pointed arch of the first stent spring lies opposite a vertex of the second stent spring arranged distally thereafter, at a distance, this vertex being less high than a highest vertex of the second stent spring; correspondingly, in this embodiment, a less low lowest point—that is to say a lowest point that is less low than a lowest low point of the first stent spring—also always comes to lie at a distance from and opposite a highest vertex of the second stent spring arranged distally thereafter, which highest vertex is higher than a less high vertex of the second stent spring.

It goes without saying that a stent spring as a whole may have different lengths of the legs of its pointed arches, or else indeed it may only have three or more than three of different lengths. The relative distances between a vertex and a lowest point or between all of the vertices and the lowest points of a stent spring may also vary.

The vascular implant according to the invention achieves the effect that there are two different bending planes between the pointed arches lying adjacently opposite, whereby the vascular implant becomes significantly more flexible, but retains its longitudinal stability. At the same time, it can be bent in a number of planes without buckling.

In conjunction with the different leg lengths, this phase arrangement of at least two, preferably all, of the stent springs of the vascular implant provides the latter with an asymmetrical pattern, whereby bending of the vascular implant according to the invention in a vessel does not lead to buckling, or this buckling is avoided to the greatest extent or can only occur in the case of significantly smaller radii, and the risk of buckling is highly decreased.

The object on which the invention is based is in this way achieved completely.

As discussed at the beginning, in the present case a "stent spring" is understood as being any annular element that—due to its material—can be compressed and, after removal of the compressive pressure, can expand again in the manner of a spring. "Meandering" is presently understood as meaning any wave-like, serpentine or looped shape of the stent spring or the stent wire, each stent spring being integrally formed as one part, i.e. from a stent spring ring circumferentially meandering. Correspondingly, a "stent spring circumferentially meandering" is in this context an annular stent element that expands and can be compressed in a spring-like manner and has a wave-like, loop-like or serpentine shape, the wave crest and wave trough alternating.

In the vascular implant according to the invention, a pointed arch is respectively formed by two legs and a vertex (in the case of a pointed arch facing toward the proximal direction) or lowest point (in the case of a pointed arch facing toward the distal direction) lying between the legs.

Due to the legs of varying length, pointed arches of varying height are obtained, their height being determined with respect to an imaginary line that runs in the circumferential direction of the stent spring and perpendicularly in relation to the longitudinal axis of the vascular implant through the highest vertex/vertices of the pointed arches facing toward the proximal direction. Due to this design and definition there are always vertices that lie under this imaginary line through the highest vertices, and consequently represent vertices that are shorter than the highest vertices. By analogy, this also applies with respect to the pointed arches or the lowest points facing toward the distal direction: here, too, an imaginary line running in the circumferential direction of a stent spring is drawn through the highest vertex/vertices of the pointed arches facing toward the distal direction, so that there are higher and shorter vertices of the pointed arches facing toward the distal direction.

Heights that can be given by way of example for the various pointed arches lie for example in the range from 4 to 18 mm, preferably about 8 mm to 14 mm, for the highest pointed arches, that is to say for the pointed arches that are higher than shorter pointed arches, and from 4 to 10 mm, preferably 6 mm to 8 mm, for the shorter pointed arches. A person skilled in the art will recognize that a stent spring can comprise, on the one hand, pointed arches with at least two or three or four or more pointed arches of varying height. If there are three pointed arches of varying height, the stent spring therefore has three different heights for the pointed arches, that is to say at least a first higher pointed arch, the height of which is the highest, at least a second pointed arch, the height of which is shorter than that of the first pointed arch, and a third pointed arch, the height of which is in turn shorter than that of the second pointed arch, etc. Heights that can be given by way of example, serving in the present case merely for exemplary purposes and not intended to be limiting, are for example 10 mm (higher pointed arches) and 8 mm (shorter pointed arches); 12 mm (higher pointed arches) and 8 mm (shorter pointed arches); 12 mm (higher pointed arches) and 9 mm (shorter pointed arches); 12 mm (higher pointed arches) and 10 mm (shorter pointed arches); 16 mm (higher pointed arches) and 14 mm (shorter pointed arches), 16 mm (higher pointed arches) and 13 mm (shorter pointed arches); 16 mm (higher pointed arches), 12 mm (shorter pointed arches) and 10 mm (still shorter pointed arches); 10 mm (higher pointed arches) and 8 mm (shorter pointed arches); 12 mm (higher pointed arches), 10 mm (shorter pointed arches) and 8 mm (still shorter pointed arches).

In the present case and throughout the description, the term "about" is intended to mean that the indications given for ranges and numbers are also intended to include those that are included by a person skilled in the art on account of measuring differences or tolerances and are suitable for achieving or helping to achieve the object on which the invention is based.

Presently, with respect to the vascular implant, the term "proximal" generally denotes that position, direction or a portion or end of a component of the vascular implant that lies closest to the heart of the patient to be treated.

Correspondingly, presently, "distal" denotes that position, direction or a portion or end of a component of the vascular implant according to the invention that is/leads further/furthest away from the heart of a patient.

Correspondingly, presently, the "proximal" end/opening and the "distal" end/opening of the vascular implant are the ends/openings by which the flow of blood through the hollow-cylindrical body of the vascular implant is ensured: when the vascular implant according to the invention is implanted in a blood vessel, such as for example the aorta, the blood coming from the heart therefore flows through the proximal end/opening of the vascular implant, and leaves the vascular implant through the distal opening thereof.

By definition, the stent springs are not directly connected to one another, and do not have any legs or struts or similar connecting elements between one another. The stent springs are only connected to one another by way of/via the implant material to which the stent springs are fixed, thereby creating an "indirect connection" between the stent springs. Therefore, stent springs successively arranged over the longitudinal axis of the vascular implant are provided at a distance from one another and do not touch one another in the unbent state of the vascular implant. The distance between the stent springs may vary and depends in particular on the intended use and the nature of the vascular implant; distances given by way of example lie between 1 mm (in the case of long points twisted in relation to one another even 0 mm) and 20 mm, advantageously 1 to 4 mm.

Furthermore, in the present case a "stent" denotes any device or a structure that provides a force of expansion and/or a supporting function due to a resilient metal frame of an implant.

Presently, and also in the prior art, the expression "stent graft" is intended to mean an implant that has a stent and also an implant ("graft") material attached thereto, which forms a lumen through at least one portion of the implant.

The vascular implant according to the invention additionally also has the effect that it allows the implant to be rotated, even in the bent state, so that three-dimensional bends can also be implemented here, without the product or implant buckling in the vessel.

With the vascular implants known in the prior art having stent springs arranged one behind the other, rotation is not possible in the bent state, since buckles occur here as a result of the symmetrical stent springs. The buckling in the case of the stent springs known in the prior art is consequently attributable to their symmetrical meandering formation and the symmetrical and successive arrangement of the stent springs over the longitudinal axis. This symmetrical arrangement of the stent springs over the longitudinal axis causes the buckling described above when the vascular implant from the prior art undergoes bending.

Furthermore, with the vascular implant according to the invention or the alternating position of the pointed arches of the stent springs, and upon loading the vascular implant into an insertion system, during which particularly the arches of the stent springs take up considerable space, advantageously, the vascular implant can be compressed to a significantly higher extend, and can thereby be loaded into small insertion catheters.

According to a further embodiment of the vascular implant according to the invention, it is preferred if at least three legs following one another directly in the circumferential direction of a stent spring have different lengths, the first leg connecting a first lowest point to a first vertex, the second leg connecting the first vertex to a second lowest point following in circumferential direction, and the third leg connects the second lowest point to a second vertex following in the circumferential direction.

According to an embodiment of the vascular implant according to the invention, it is preferred if the pointed arches facing toward the proximal direction are respectively formed by two legs of the same length, and if in the circumferential direction of the stent spring a higher pointed arch facing toward the proximal direction respectively alternates with a shorter pointed arch facing toward the proximal direction. With this embodiment, therefore, a higher pointed arch facing toward the proximal direction always alternates with a pointed arch facing toward the proximal direction that is shorter than the higher pointed arch; the shorter pointed arch is followed again by a higher pointed arch facing toward the distal direction, which may be as high as the higher pointed arch before the shorter pointed arch, etc. Due to the design of the stent spring, i.e. on account of the fact that a pointed arch facing toward the proximal direction always shares a leg with a pointed arch facing toward the distal direction that follows directly thereafter, the pointed arches facing toward the distal direction of this embodiment are formed, respectively, by two legs of different lengths.

The pointed arches facing toward the distal direction are, thus, all of the same height, so that this stent spring is suitable in particular for attachment as a terminal stent spring at the distal end of the vascular implant.

In a further embodiment, it is preferred if, in circumferential direction of the stent spring, a higher pointed arch facing toward the proximal direction x respectively alternates with a shorter pointed arch facing toward the proximal direction x, and a higher pointed arch facing toward the distal direction y respectively alternates with a shorter pointed arch facing toward the distal direction y.

In yet another embodiment, it is preferred if at least one stent spring, in its circumferential direction, has the pointed arches facing toward the proximal and/or distal direction x or y formed such, that a high pointed arch is followed by a shorter pointed arch, and the shorter pointed arch is followed by a pointed arch that is shorter than the previously arranged shorter pointed arch, and this is again followed by a higher pointed arch, and so on. In this embodiment, consequently, virtually a "triple pattern" comprising a high pointed arch, a shorter pointed arch and a still shorter pointed arch follows just such a triple pattern, whereby, by definition, again an asymmetrical stent spring is provided.

According to a still further embodiment, it may be preferred if in at least one stent spring, in its circumferential direction, the pointed arches facing toward the proximal direction are all of the same height and alternate with pointed arches of varying height facing in the distal direction.

With the various embodiments presented above, the asymmetrical stent springs and asymmetrical stent-spring arrangements according to the invention can be achieved.

According to a further embodiment, it is preferred if the distance $z1$ between a first vertex and a first lowest point following the first vertex in the circumferential direction of at least one stent spring differs from the distance $z2$ between the first lowest point and a second vertex following the first lowest point in the circumferential direction of the same stent spring.

This embodiment has the advantage that an additional asymmetry can be created, by means of which buckling of the vascular implant can be further reduced.

According to an embodiment of the vascular implant according to the invention, it is preferred if the self-expanding vascular implant according to the invention has at least three stent springs, successively arranged in the longitudinal direction, that are not directly connected to one another, but only connected to one another via the implant material.

According to a further embodiment, it is preferred if the vascular implant according to the invention has between three and ten, preferably three, four, five, six, seven, eight, nine or ten, stent springs arranged one behind the other.

The number of stent springs will depends on the required length of the vessel implant to be used, or on the vascular defects of a patient, which are to be bridged.

Also, the number of vertices and lowest points of a vascular implant according to the invention, or the pointed arches alternately facing toward the proximal direction and the distal direction, will depend on the diameter of the vessel or portion of a vessel to be treated. Thus, for example, with a vascular implant that is used in the arterial vascular system of an adult patient, it is preferred if it has between six and twelve pointed arches facing toward the proximal direction and between six and twelve pointed arches facing toward the distal direction.

It goes without saying that the surgeon performing the treatment, on the basis of the diameter of the vessel and the extent of the vascular region to be treated, can preset the dimensions on the basis of which the optimal number of stent springs, and also number of pointed arches or vertices and lowest points can be determined.

With the vascular implant according to the invention, the stent springs are fixed to the implant material at a specific distance from one another. The stent springs are preferably sewn on or adhesively attached. The distance between the stent springs successively arranged over the longitudinal axis is such that the vascular implant has sufficient overall stability with at the same time good bendability. Thus, the distance between two stent springs successively arranged in the longitudinal direction, measured between the lowest lowest point of the first stent spring and the highest vertex of the second stent spring arranged distally thereafter, is from between about 0 mm to about 5 mm—whereby the lowest lowest point and the highest vertex do not necessarily lie directly opposite one another.

According to a preferred embodiment of the self-expanding vascular implant according to the invention, the stent springs consist of a self-expanding material, preferably nitinol.

Nitinol is the material currently used most frequently for self-expanding vascular implants with stent springs. Nitinol has the advantage that it has "shape-memory" properties, which means that stent springs of nitinol are produced in the expanded state, can be compressed for insertion into the vessel, and after removal of a compression means, generally a withdrawal sheath, the stent springs again return into the expanded initial state of their own accord due to the "shape-memory" properties. As a result, the vascular implant, as a whole, settles against the vessel wall and is pressed against the vessel wall on account of the spring action of the stent springs, so that it is securely anchored in the vessel.

As already mentioned further above, it is preferred if the stent springs are sewn onto the implant material at a distance from one another and one behind the other over the longitudinal axis of the vascular implant.

This measure has the advantage that the stent springs can be individualized and even fastened to the implant material at different distances from one another, so that for example two stent springs arranged one behind the other have a greater distance from one another than two other stent springs situated further distally or further proximally. In this way, the vascular implant can be adapted to the vessel portion to be treated, whereby the vascular implant can also have, e.g., fenestrations over its longitudinal axis and/or over its circumference, which fenestrations represent openings for outgoing vessels in the region to be treated. The provision of fenestrations in the implant material—usually in connection with side branches extending from the vascular implant—ensures the blood supply to the vessel branching off in this region, even after introduction of the vascular implant into a vessel.

It goes without saying that the fenestration in the implant material is provided between two stent springs arranged one behind the other. In this case, either the fenestration may be adapted to the distance between the two stent springs, or else the distance of the two stent springs from one another may be adapted to the size of the fenestration. Also, several fenestrations may be provided circumferentially on the implant material between two stent springs arranged one behind the other, and several fenestrations may be distributed over the longitudinal axis of the vascular implant.

One skilled in the art will recognize at which points of the vascular implant according to the invention the fenestrations must be provided, and will be able to provide them in accordance with the specific nature of the respective vessel.

With the vascular implant according to the invention it is preferred, if the implant material comprises a material that is selected from polyester, polyurethane, polystyrene, polytetrafluoroethylene or ultrahigh molecular weight polyethylene (UHMPE), or mixtures thereof.

The use of these materials as such is known in medicine, in particular also for vascular implants, so that a person skilled in the art can choose suitable materials for the specific use of the vascular implant on the basis of his knowledge.

The present invention therefore also relates to a further embodiment of the vascular implant according to the invention that is formed in such a way that there is—besides the at least one hollow-cylindrical body—also at least one branching side body, which branches off from the hollow-cylindrical body of the vascular implant. The side body as such is a hollow-cylindrical body comprising stent springs successively arranged with an implant material connecting them, the side bodies being intended for vessels branching off from a main vessel. The side bodies generally have a smaller diameter than the "main body" of the vascular implant.

The at least one side body may consist of a stented portion—i.e. a portion that has stent springs or a stent wire mesh—or may have such a portion, or else may have an unstented portion, consisting only of implant material, or consist of such a portion. The materials of which the side body consists are generally also those from which the main body is made.

It may also be preferred in a particular embodiment of the vascular implant according to the invention if the vascular implant has different diameters over its longitudinal direction.

This embodiment has the advantage that it can be used for example in narrowing or tapering vessels or else in vessels that branch off, such as for example in the bifurcation of the aorta.

Further advantages and features will be apparent from the following description and the accompanying drawing.

It goes without saying that the features mentioned above and still to be explained below can be used not only in the combination respectively specified, but also in other combinations or on their own without departing from the scope of the present invention.

BRIEF DESCRIPTION OF THE DRAWINGS

An exemplary embodiment of the invention is shown in the drawing and is described in more detail below with reference thereto. In the drawing.

DESCRIPTION OF PREFERRED EMBODIMENTS

Figure 1:
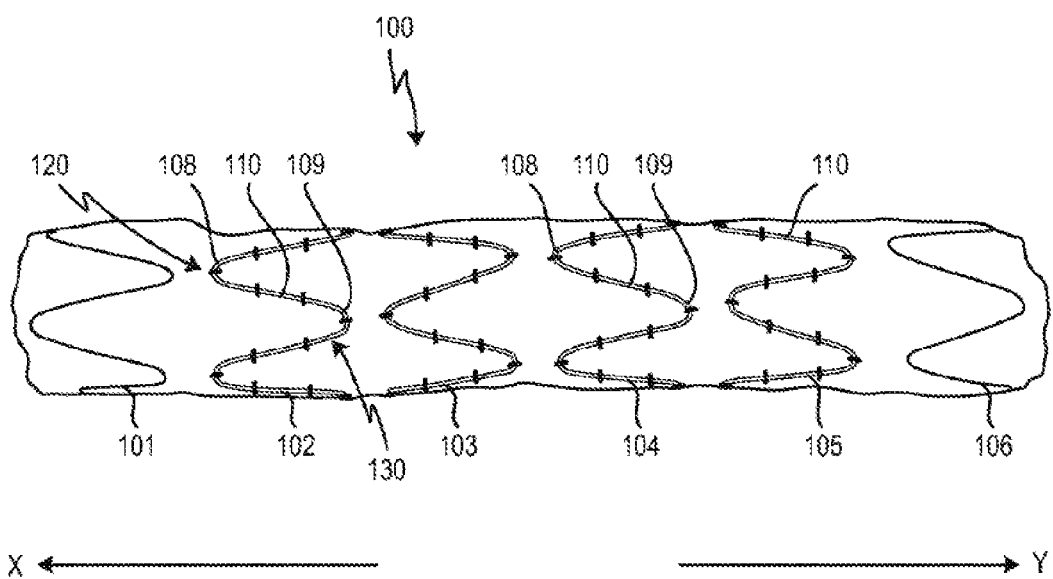
FIG. 1 shows an exemplary embodiment of a vascular implant of the prior art in the non-bent form.

FIG. 1 shows a self-expanding vascular implant, as known in the prior art. This vascular implant 100 has stent springs 101, 102, 103, 104, 105, 106 arranged one behind the other in the longitudinal direction, which respectively have vertices 108 and lowest points 109, or pointed arches 120 facing toward the proximal direction x and pointed arches 130 facing toward the distal direction y.

As FIG. 1 shows, the vertices 108 of a stent spring 101, 102, 103, 104, 105, 106 are connected, respectively, by way of legs 110 to lowest points 109 of the same stent spring 101, 102, 103, 104, 105, 106, and the lowest points in turn by way of legs 110 to the vertex 108 following thereafter. FIG. 1 also shows that the course alternating between vertex and lowest point leads to a symmetrical meandering shape of the stent spring 101, 102, 103, 104, 105, 106. The stent springs 101 to 106 are attached to an implant material 112, and more precisely in such a way that the stent springs 101 to 106 are arranged symmetrically: on the one hand, the legs of all the stent springs 101, 102, 103, 104, 105, 106, which respectively connect vertex 108, lowest point 109, vertex 108, lowest point 109, etc. of a stent spring 101, 102, 103, 104, 105, 106 to one another, are of the same length, so that the vertices 108 and lowest points 109 circumferentially are at the same height—or, that is to say, are at the same amplitude. On the other hand, the stent springs arranged one behind the other over the longitudinal axis of the vascular implant of the prior art are arranged at a distance from one another in such a way that a lowest point 109 of the stent spring 101 lies opposite the vertex 108 of the distally situated stent spring 102, without them directly touching or being directly connected to one another. Correspondingly, in turn a lowest point 109 of the second stent spring 102 is also directly assigned to a vertex 108 of the distally situated stent spring 103, so that these two points of the two stent springs 102, 103 lie opposite one another, with a distance between the two stent springs 102, 103, too. Due to this arrangement, an overall symmetrical pattern or symmetrical arrangement of the stent springs 101, 102, 103, 104, 105, 106 arranged over the longitudinal axis of the vascular implant 100 is obtained.

Embodiments of the vascular implant according to the invention are described below. One embodiment is shown schematically and not drawn to scale in FIGS. 2A and 2B.

Figure 2A:
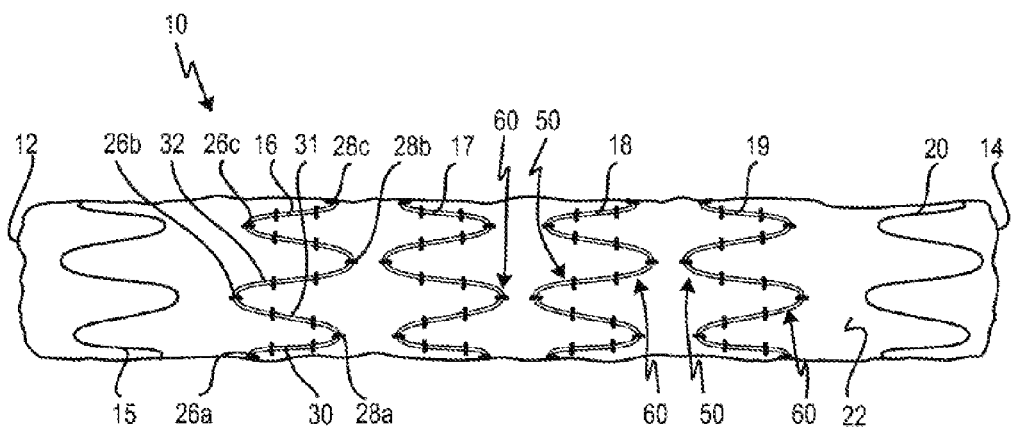
FIG. 2A shows an embodiment of the vascular implant according to the invention in the non-bent state.

The embodiment of the vascular implant 10 according to the invention that is represented in FIG. 2A has a proximal end 12 and a distal end 14, and has stent springs 15, 16, 17, 18, 19, 20 successively arranged one behind the other over the longitudinal axis that are, respectively, not directly connected to one another, but only by way of the implant material 22, thus forming a hollow-cylindrical body 24.

The stent springs 15 to 20, respectively, are integrally formed, i.e. as one part, and are circumferentially formed in waves or loops, and consequently extend in a meandering manner over the circumference of the vascular implant 10. Also in FIG. 2, the proximal direction is identified by x and the distal direction by y, and also by way of arrows pointing in the respective direction. According to the invention, the stent springs 15, 16, 17, 18, 19, 20 of the vascular implant 10 have pointed arches 50, facing toward the proximal direction x, and pointed arches 60, facing toward the distal direction y, not all of the pointed arches being provided with reference numerals, but only, and by way of example, two pointed arches 50 and 60, respectively, of the stent springs 18 and 19, for the sake of clarity. In other words, the pointed arches 50, 60 of the stent springs form circumferential waves with wave crests, which correspond to the pointed arches 50, and wave troughs, which correspond to the pointed arches 60.

The individual stent springs 15 to 20, respectively, have vertices 26a, 26b, 26c and lowest points 28a, 28b, 28c, wherein with "vertices", presently, the highest point of a wave/the wave crest, when seen toward the proximal direction, is designated, and with "lowest point" the lowest point of a wave/the wave trough is designated. Here, too, for the sake of clarity, not all of the vertices and lowest points of all the stent springs have been provided with reference signs. The vertices 26a, 26b, 26c therefore respectively represent the highest point of the pointed arches 50 facing toward the proximal direction x, and the lowest points 28a, 28b, 28c respectively represent the highest point of the pointed arches 60 facing toward the distal direction y.

As FIG. 2 reveals, the stent springs 16, 17, 18, 19 are sewn onto the implant material 22 by way of sutures 40.

Generally—and as already mentioned further above—when referring to self-expanding vascular implants or stent grafts or endoluminal implants, the terms "distal" and "proximal" are—generally and presently—used to denote the respective ends of the vascular implants, the term "distal" denoting the part or the end that lies further downstream with respect to the bloodstream. The term "proximal", on the other hand, denotes, again with respect to the bloodstream, a part or the end that lies further upstream with respect to the bloodstream. In other words, the term "distal" means toward the direction of the bloodstream, and the term "proximal" means opposite to the direction of the bloodstream. By contrast, when referring to catheters or insertion systems for self-expanding vascular implants, the term "distal" denotes the end of the catheter or insertion system that is inserted into the patient, or that is furthest away as seen from the user of the catheter/insertion system; and the term "proximal" denotes the end of the catheter/insertion system that is closer to the user.

Figure 2B:
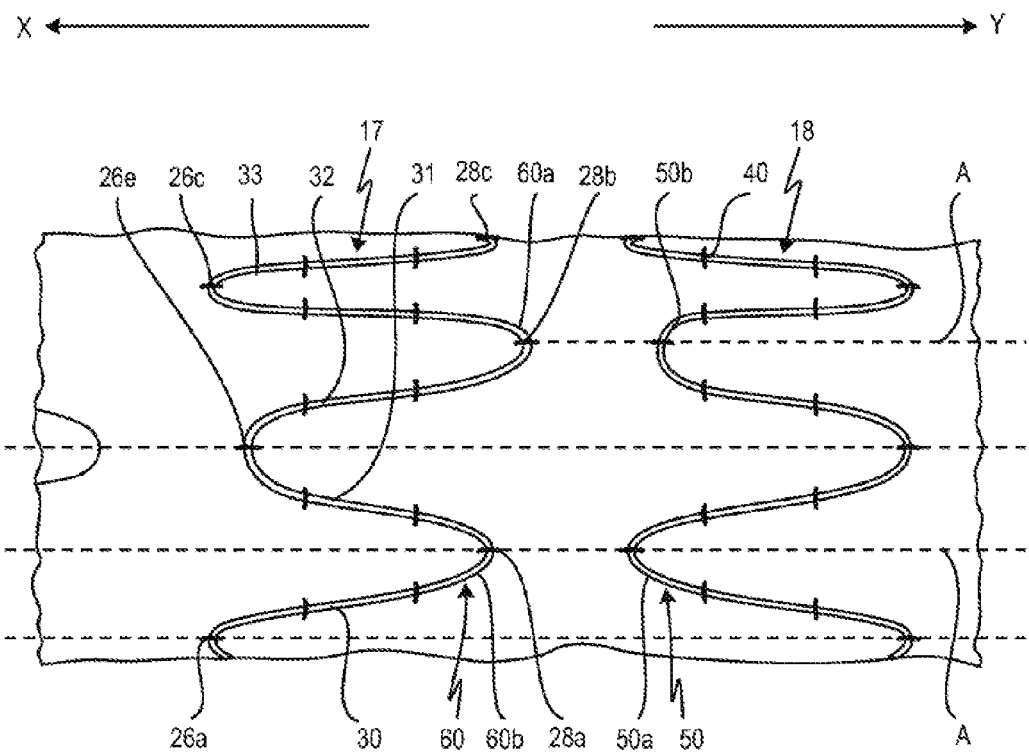
FIG. 2B shows an enlarged portion of the vascular implant according to the invention from FIG. 2A.

FIG. 2A, and, in an enlarged representation of a portion, FIG. 2B, show that at least one of the stent springs 15 to 20 has legs 30, 31, 32, 33 which—respectively-connect a first lowest point 28a with a first vertex 26a, this vertex with a second lowest point 28b, this lowest point 28b with a second vertex 26b, and this vertex 26b with a third lowest point 28c, and this lowest point 28c in turn with the vertex 26c. The legs 30, 31, 32 have different lengths, thereby forming pointed arches 50, 60 with different heights (see also FIG. 4). As a result, an overall asymmetrical shape of the pointed arches or "waves" of the stent springs 15, 16, 17, 18, 19, 20 is achieved, thereby effecting a reduced buckling.

FIGS. 2A and 2B also show that the stent springs 17 and 18 are arranged in relation to one another in such a way that a higher pointed arch 50a facing toward the proximal direction x, of a first stent spring 18 lies opposite a shorter pointed arch 60b facing toward the distal direction y, of a second stent spring 17 arranged thereafter in the proximal direction x, at a distance and at an imaginary line (A) that is parallel to the longitudinal axis of the vascular implant 10. Similarly, a shorter pointed arch 50b, facing toward the proximal direction x, of a first stent spring 18 lies opposite a higher pointed arch 60a, facing in the distal direction y, of a second stent spring 17 arranged thereafter in the proximal direction x, at a distance and at an imaginary line (A) that is parallel to the longitudinal axis of the vascular implant 10.

In conjunction with the asymmetrical meandering shape of the individual stent springs 15, 16, 17, 18, 19, 20—this arrangement provides the vascular implant aso with an asymmetrical arrangement with respect to the individual stent springs 15, 16, 17, 18, 19, 20 in relation to one another, and this further asymmetrical design further enhances the effect of avoiding buckling.

Figure 3A:
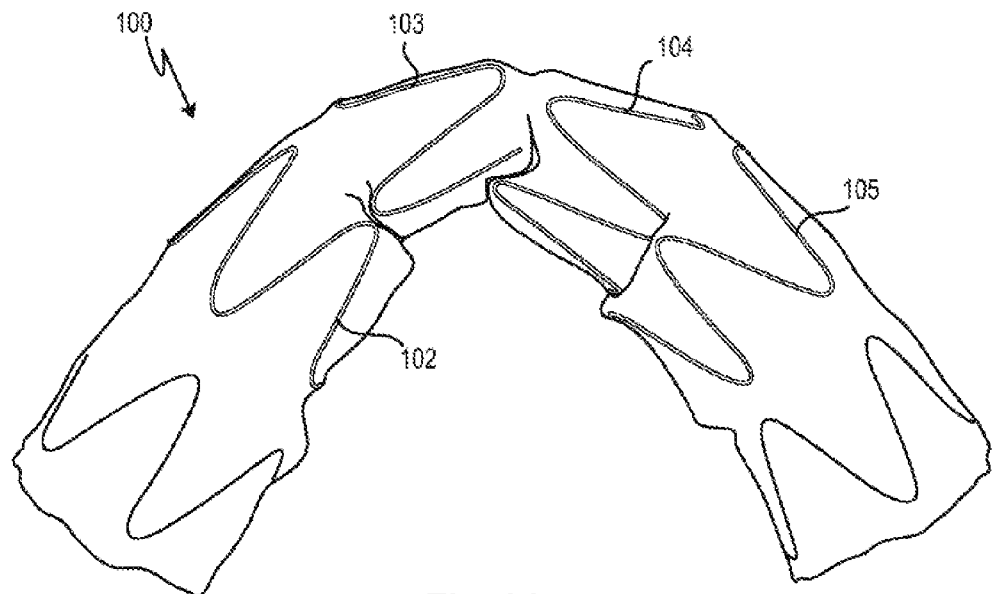
FIG. 3A shows a drawing of the exemplary embodiment of the vascular implant of the prior art in the bent state.

The effect of avoiding buckling is graphically represented in FIG. 3: here, a vascular implant 100 that is known in the prior art and has been put into a bent state is shown in FIG. 3A. The vascular implant 100 known in the prior art is badly buckled at the bend, which can decisively impair the blood flow through the vessel.

Figure 3B:
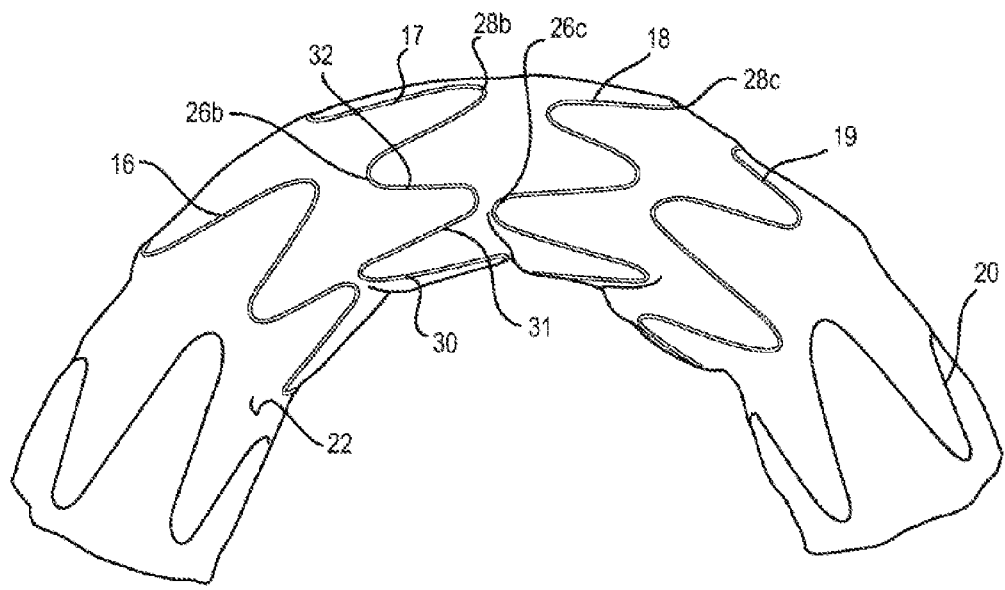
FIG. 3B shows the exemplary embodiment of the vascular implant according to the invention from FIG. 2A, likewise in the bent state.

By contrast, the embodiment according to the invention of the vascular implant 10, as it is represented in FIG. 3B, does not exhibit any buckling in the bent state; here there are formed, at most, small creases in the implant material 22, but not a buckle between two stent springs 15, 16, 17, 18, 19, 20 arranged one behind the other, as in the case of the vascular implant 100 known in the prior art.

Figure 4A:
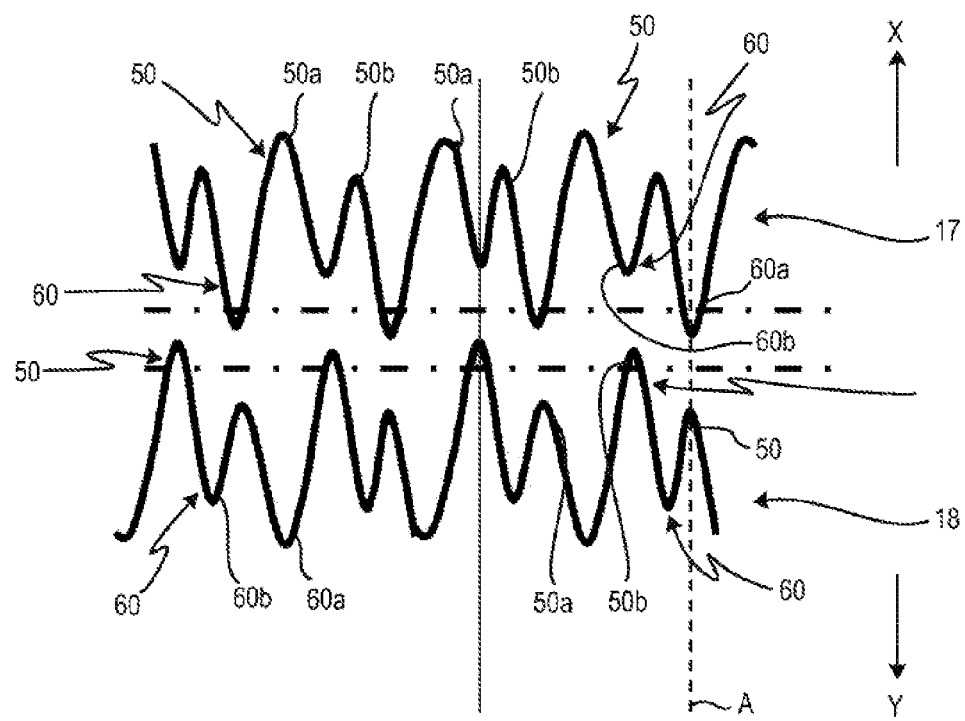
FIGS. 4A-4B show a schematic drawing of an exemplary design and arrangement of two stent springs arranged one behind the other of a vascular implant according to the invention, with A: two different heights for the pointed arches facing toward the proximal direction or the distal direction; and with B: three different heights for the pointed arches facing in the proximal direction or the distal direction, respectively.
Figure 4B:
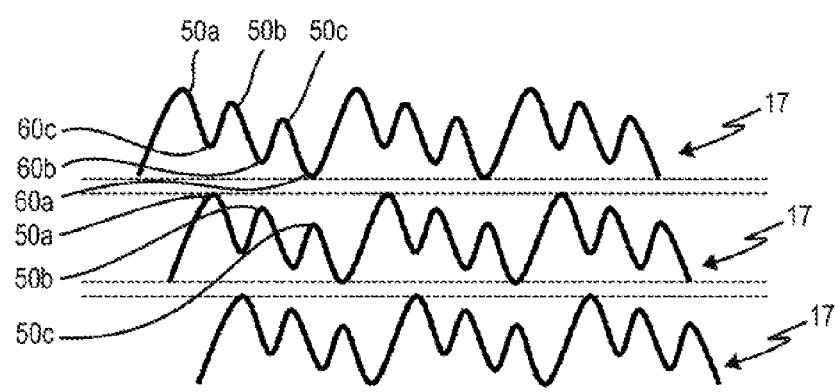

FIG. 4 additionally shows two exemplary schematic designs and arrangements of two (or three) downstream stent springs 17 and 18 (FIG. 4A) and 17, 18 and 19 (FIG. 4B). Here, the same reference numbers are used for denoting the same features as in FIGS. 1 to 3.

FIG. 4A shows the asymmetrical meandering shape of the two stent springs 17 and 18 of the exemplary embodiment of the vascular implant according to the invention: the stent springs 17 and 18 have alternating pointed arches 50 facing toward the proximal direction x and pointed arches 60 facing toward the distal direction y. The pointed arches 50 facing toward the proximal direction x alternately comprise high or higher pointed arches 50a and shorter pointed arches 50b, which are shorter than the pointed arches 50a facing toward the proximal direction x that are respectively arranged before them. Furthermore, the stent springs 17 and 18 respectively comprise pointed arches 60 facing in the distal direction y, with higher pointed arches 60a and shorter pointed arches 60b. In this case, the two stent springs 17, 18 are arranged with respect to their pointed arches such, that a higher pointed arch 60a, facing toward the distal direction x, of the stent spring 17 lies opposite a shorter pointed arch 50b of the stent spring 18 arranged thereafter in the distal direction y at a distance and at an imaginary line A that is parallel to the longitudinal axis of the vascular implant, or perpendicularly in relation to the circumference of the stent springs 17, 18.

FIG. 4B reveals a further embodiment: here, three pointed arches of varying height facing toward the proximal direction x alternate in such a manner that a higher facing pointed arch 50a is adjoined by a shorter pointed arch 50b, and the latter is adjoined by a pointed arch 50c, which is even shorter than the pointed arch 50b; this is in turn adjoined by a higher pointed arch 50a, which in turn is followed by a shorter pointed arch 50b, and so on. Due to this design, the pointed arches 60 facing toward the distal direction y are in the circumferential direction of the stent spring 17 such, that a shorter pointed arch 60c is followed by a pointed arch 60b that is higher than the pointed arch 60c, and this pointed arch 60b is followed by a higher pointed arch 60a, which is higher than the pointed arch 60b. The pointed arches 50b and 60b therefore, respectively, have heights that lie between the heights of the higher pointed arch and the shorter pointed arch 50*a* and 50*c* and 60*a* and 60*c*, respectively.

With the vascular implant according to the invention, the two stent springs 17 and 18 are arranged one after the other, such, that the higher pointed arch 50*a*, facing toward the proximal direction, of the stent spring 18 lies opposite the shorter pointed arch 60*c*, facing toward the distal direction, of the stent spring 17, the pointed arch 50*b* of the stent spring 18 lies opposite the pointed arch 60*b* and the shorter pointed arch 50*c*, facing toward the proximal direction, of the stent spring 18 lies opposite the higher pointed arch 60*a*, facing toward the distal direction, of the stent spring 17. The stent springs 17, 18 and 19 shown in FIG. 4B and schematically arranged one behind the other allow the overall asymmetrical arrangement to be well recognized.

Figure 5:
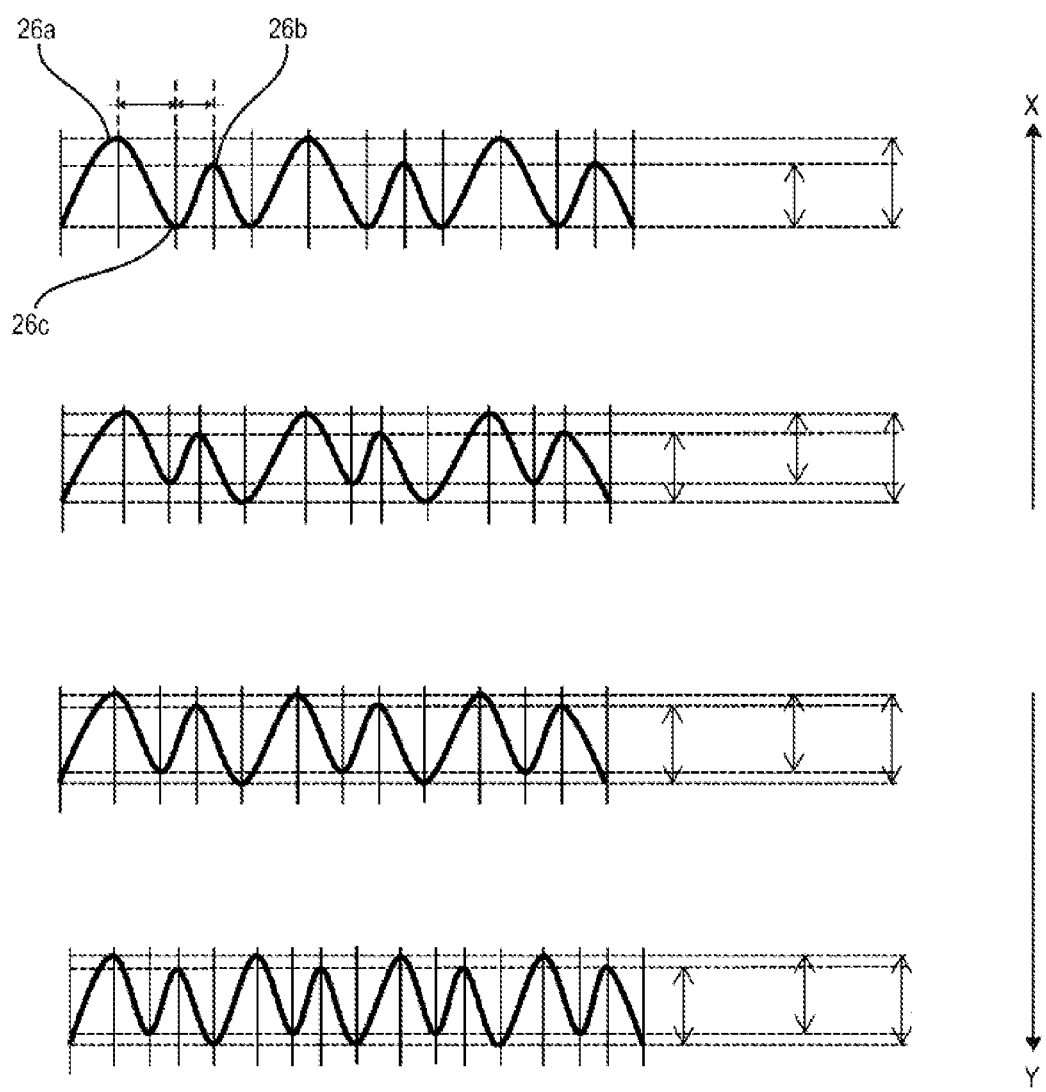
FIG. 5 shows a schematic drawing of exemplary course of stent springs, for use in vascular implants according to the invention.

FIG. 5 finally shows various designs of stent springs that are suitable for the purposes of the present application, having asymmetrically formed pointed arches with different heights. With the asymmetrical arrangement according to the invention of such stent springs in relation to one another and in successive sequence, and in combination with the individual asymmetrical stent springs a vascular implant can be formed by means of which buckling in a vessel, as described herein, can be advantageously avoided.

The exemplary shapes of stent springs represented in the four embodiments in FIG. 5 show different variations and possibilities for the forming of asymmetrical stent springs, whereby two different heights of the pointed arches facing toward the proximal direction x and toward the distal direction y are depicted in the upper three embodiments, whereas the stent spring right at the bottom in FIG. 5 respectively has three different heights of the pointed arches.

Furthermore, the two upper stent springs shown in FIG. 5 show that the two different heights of the pointed arches respectively facing toward the distal direction and the proximal direction can also have different values: thus, in the uppermost example shown in FIG. 5, the difference between the heights of the pointed arches is greater than in the second-uppermost example.

Furthermore, the number of pointed arches of a stent spring can be governed by the distance between the pointed arches respectively facing toward the proximal direction x and the distal direction y: the smaller the distance, the more pointed arches a stent spring can have, which can be seen in particular from the third example.

Finally, a shape with three different heights respectively of the pointed arches facing toward the proximal and distal directions is shown in the lowermost example.

The uppermost example in FIG. 5 also shows that the distance z1 between a first vertex 26*a* and a first lowest point 28*a* following the first vertex 26*a* in the circumferential direction of at least one stent spring differs from the distance z2 of the first lowest point 28*a* from a second vertex 26*b* following the first lowest point 28*a* in the circumferential direction of the same stent spring. As a result, a further asymmetry can be achieved.

What is claimed is:

1. A self-expanding vascular implant for implanting into a blood vessel, the vascular implant having a hollow-cylindrical body with a proximal end, a distal end, and a longitudinal axis, and comprising:

stent springs that are successively arranged at a distance over its longitudinal axis and which circumferentially meander, respectively, and an implant material fixed to the stent springs and connecting them, the stent springs being connected by way of the implant material only and not between one another, and the circumferential stent springs having pointed arches facing alternately toward the proximal direction (x) and the distal direction (y), which are connected to one another by way of legs, the stent springs defining a corresponding circumferential area of the implant material around a corresponding stent spring, wherein at least three stent springs successively arranged in the longitudinal direction, respectively, have legs of different lengths for forming of circumferentially arranged pointed arches of varying height, with a plurality of higher and shorter pointed arches facing both, in the proximal direction (x) and in the distal direction (y), wherein at least two of the higher pointed arches facing in the proximal direction of each of the at least three stent springs have a same height, and wherein at least two of the shorter pointed arches facing the proximal direction have a same height, wherein at least three legs successively arranged in the circumferential direction of a stent spring, respectively, have different lengths, and wherein, in an expanded state, a higher pointed arch facing toward the proximal direction (x) of a first stent spring of the at least three stent springs lies opposite a shorter pointed arch facing toward the distal direction (y), of a second stent spring of the at least three stent springs arranged in the proximal direction (x) thereafter, at a distance and at an imaginary line (A) that is parallel to the longitudinal axis of the vascular implant, and/or in that a shorter pointed arch facing toward the proximal direction (x), of a first stent spring lies opposite a longer pointed arch facing toward the distal direction (y) of a second stent spring arranged thereafter in the proximal direction (x), at a distance and at an imaginary line (A) that is parallel to the longitudinal axis of the vascular implant, such, that no pointed arch of a stent spring successively arranged after another stent spring is attached within the corresponding circumferential area of an adjacent stent spring.

2. The self-expanding vascular implant as claimed in claim 1, wherein in the proximal direction (x), the circumferentially arranged pointed arches of varying height include at least one intermediate pointed arch, the at least one intermediate pointed arch having a height that is less than height of the higher pointed arches and greater than the height of the shorter pointed arches, and wherein, in the circumferential direction of the stent spring, a higher pointed arch facing toward the proximal direction (x) respectively alternates with one or more of the shorter pointed arches and the at least one intermediate pointed arch.

3. The self-expanding vascular implant as claimed in claim 1, wherein in the proximal direction (x), the circumferentially arranged pointed arches of varying height include at least one intermediate pointed arch, the at least one intermediate pointed arch having a height that is less than height of the higher pointed arches and greater than the height of the shorter pointed arches, and wherein in at least one stent spring, in the circumferential direction, the pointed arches facing toward the proximal direction (x) are formed such, that a higher pointed arch is followed by an intermediate pointed arch, and the intermediate pointed arch is followed by a shorter pointed arch, and this is again followed by a higher pointed arch.

4. The self-expanding vascular implant as claimed in claim 1, wherein the distance (z1) between a first pointed arch facing in the proximal direction and a first pointed arch facing in the distal direction following the first pointed arch facing in the proximal direction in the circumferential direction of at least one stent spring differs from the distance (z2) between the first pointed arch facing in the distal direction and a second pointed arch facing in the proximal direction following the first pointed arch facing in the distal direction in the circumferential direction of the same stent spring.

5. The self-expanding vascular implant as claimed claim 1, wherein it has between 6 and 12 pointed arches facing toward the proximal direction (x) and between 6 and 12 pointed arches facing toward the distal direction (y).

6. The self-expanding vascular implant as claimed in claim 1, wherein it has at least three stent springs successively arranged one behind the other over the longitudinal axis.

7. The self-expanding vascular implant as claimed in claim 1, wherein it has between three and ten stent springs successively arranged one behind the other.

8. The self-expanding vascular implant as claimed in claim 1, wherein the stent springs are sewn onto the implant material at a distance from one another.

9. The self-expanding vascular implant as claimed in claim 1, wherein it is formed as a vascular implant comprising at least one side body branching off from the hollow-cylindrical body.

10. A self-expanding vascular implant for implanting into a blood vessel, the vascular implant having a hollow-cylindrical body with a proximal end, a distal end, and a longitudinal axis, and comprising:
    stent springs that are successively arranged at a distance over its longitudinal axis and which circumferentially meander, respectively, and
    an implant material fixed to the stent springs and connecting them, the stent springs being connected by way of the implant material only and not between one another, and the circumferential stent springs having pointed arches facing alternately toward the proximal direction (x) and the distal direction (y), which are connected to one another by way of legs, the stent springs defining a corresponding circumferential area of the implant material around a corresponding stent spring,
    wherein each of the stent springs that are successively arranged in the longitudinal direction, respectively, have legs of different lengths for forming of circumferentially arranged pointed arches of varying height, with a plurality of higher and shorter pointed arches facing both, in the proximal and in the distal direction, wherein at least two of higher pointed arches facing in the proximal direction of each of the at least three stent springs have a same height, and wherein at least two of shorter pointed arches facing the proximal direction have a same height,
    wherein at least three legs successively arranged in the circumferential direction of a stent spring, respectively, have different lengths, and
    wherein, in an expanded state, a higher pointed arch facing toward the proximal direction (x) of a first stent spring of the at least three stent springs lies opposite a shorter pointed arch facing toward the distal direction (y), of a second stent spring of the at least three stent springs arranged in the proximal direction (x) thereafter, at a distance and at an imaginary line (A) that is parallel to the longitudinal axis of the vascular implant, and in that a shorter pointed arch facing toward the proximal direction (x), of a first stent spring lies opposite a longer pointed arch facing toward the distal direction (y) of a second stent spring arranged thereafter in the proximal direction (x), at a distance and at an imaginary line (A) that is parallel to the longitudinal axis of the vascular implant, such that no pointed arch of a stent spring successively arranged after another stent spring is attached within the corresponding circumferential area of an adjacent stent spring.

11. The self-expanding vascular implant of claim 10, wherein in the proximal direction (x), the circumferentially arranged pointed arches of varying height include at least one intermediate pointed arch, the at least one intermediate pointed arch having a height that is less than height of the higher pointed arches and greater than the height of the shorter pointed arches.

\* \* \* \* \*